United States Patent [19]
Mathieu

[11] Patent Number: 5,632,897
[45] Date of Patent: May 27, 1997

[54] METHOD FOR REMOVING ALUMINUM IONS FROM BLOOD

[75] Inventor: Bernd Mathieu, Spiesen-Elversberg, Germany

[73] Assignee: Fresenius AG, Bad Homburg, Germany

[21] Appl. No.: 464,568

[22] Filed: Jun. 5, 1995

Related U.S. Application Data

[62] Division of Ser. No. 119,908, Sep. 10, 1993, abandoned.

[30] Foreign Application Priority Data

Sep. 11, 1992 [DE] Germany .......................... 42 30 513.6

[51] Int. Cl.$^6$ .................... B01D 61/24; B01D 21/01; A61M 1/14
[52] U.S. Cl. .................... 210/645; 210/646; 210/723; 210/726; 210/727; 210/728; 210/729; 210/732
[58] Field of Search .................... 210/645, 646, 210/696, 698, 723, 726, 727, 728, 729, 732; 252/1; 424/682; 514/836, 56, 822; 604/4, 5

[56] References Cited

U.S. PATENT DOCUMENTS

| | | | |
|---|---|---|---|
| 4,203,891 | 5/1980 | Rock | 530/383 |
| 4,209,392 | 6/1980 | Wallace | 210/646 |
| 4,359,463 | 11/1982 | Rock | 424/529 |
| 4,500,309 | 2/1985 | Diederich et al. | 210/646 |
| 4,695,460 | 9/1987 | Holme | 435/2 |
| 4,728,430 | 3/1988 | Dileo et al. | 210/651 |
| 4,863,964 | 9/1989 | Hedlund et al. | 514/54 |
| 4,925,665 | 5/1990 | Murphy | 424/532 |
| 5,057,226 | 10/1991 | Antwiler | 210/645 |
| 5,211,849 | 5/1993 | Kitaevich et al. | 210/646 |

FOREIGN PATENT DOCUMENTS

| | | |
|---|---|---|
| 4004978 | 8/1991 | Germany . |
| 9106326 | 5/1991 | WIPO . |

OTHER PUBLICATIONS

A. Hümpfner, "Aluminumintoxikation bei Niereninsuffzienz," W. Zuckschwerdt Verlag, München (1989); pp. 144–145.

ASAIO Transactions, Bd. 34, No. 3, Jul. 1988, Hagertown, Md., U.S., "Citrate for Regional Anticoagulation, Effects on Blood.PO$_2$, Ammonia, and Aluminum", pp. 524–527.

*Primary Examiner*—John Kim
*Attorney, Agent, or Firm*—Whitham, Curtis, Whitham & McGinn

[57] ABSTRACT

A method for removing aluminum from blood includes the step of adding to the blood an anticoagulant and a complexing agent for aluminum or one compound effective in both preventing coagulation of blood and capable of complexing aluminum. The complexing agent or compound capable of complexing aluminum is allowed to intermingle with the blood and complex with aluminum present in the blood. The complex of complexing agent and aluminum formed during the intermingle step is then separated using a semipermeable membrane, and the blood is recovered. The method is particularly useful in treating patient's having aluminum intoxication.

11 Claims, 1 Drawing Sheet

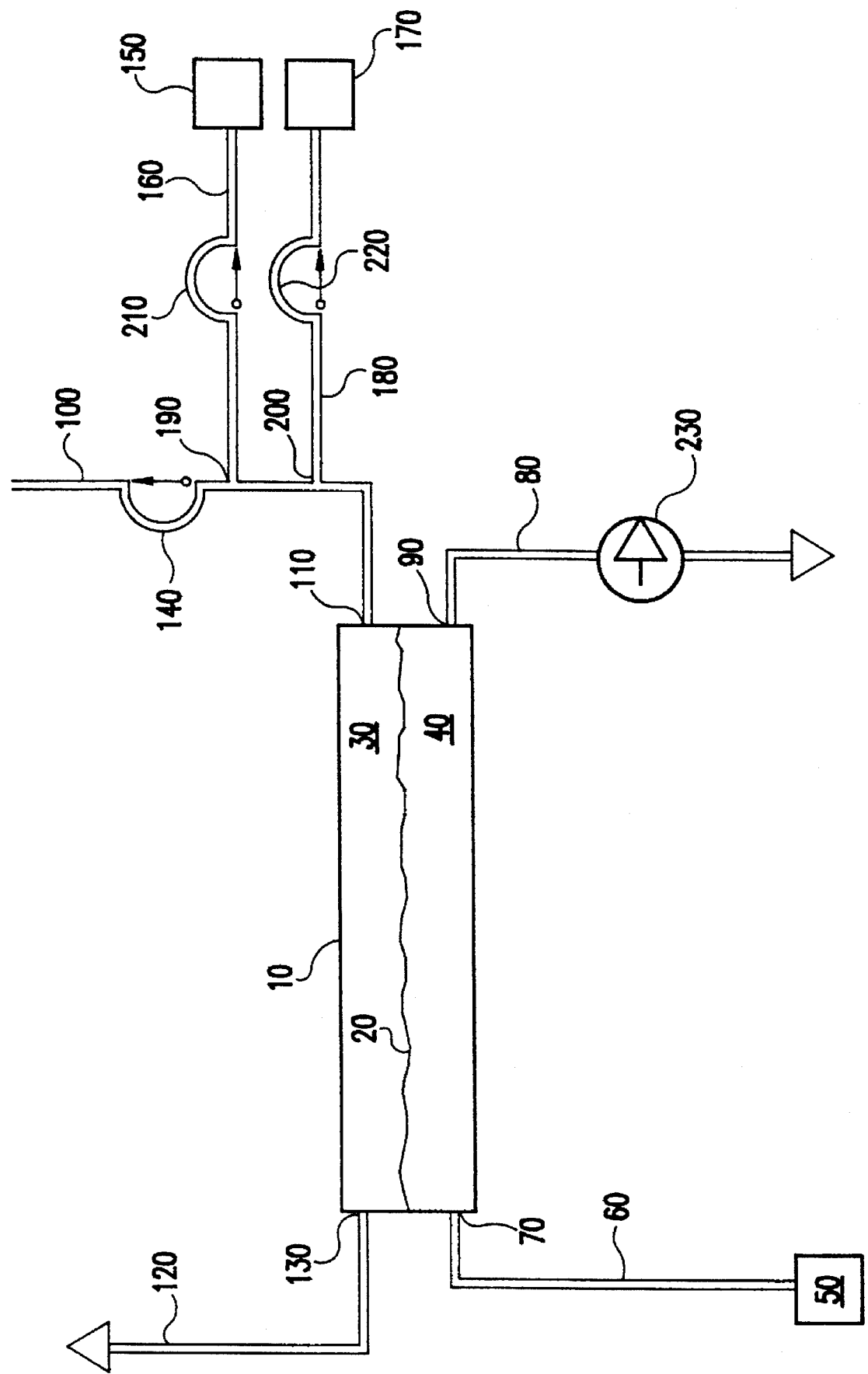

METHOD FOR REMOVING ALUMINUM IONS FROM BLOOD

CROSS REFERENCE TO RELATED APPLICATION

This application is a divisional of application Ser. No. 08/119,908 filed Sep. 10, 1993, abandoned.

BACKGROUND OF THE INVENTION

The present invention concerns an apparatus and a solution for removing aluminum ions from blood. For more than 20 years it has been known that aluminum is deposited in the bones of dialysis patients and that it is therefore necessary to keep aluminum away from the bodies of such patients or to remove it therefrom.

In healthy persons aluminum is excreted almost exclusively through the kidneys. Patients lacking their own kidney function cannot perform this excretion. They accumulate the aluminum in the body if the intake of aluminum exceeds the excretion carried out by means of the dialysis treatment conventionally performed three times per week.

The main sources of aluminum intake are aluminum hydroxide based phosphate binders, drinking water, food prepared or stored in aluminum receptacles and a range of pharmaceuticals.

The excretion of aluminum through the membrane of a dialyzer during dialysis is usually relatively minimal. Thus, even in modern open-pore high-flux dialyzers a reduction of only 40% of the aluminum level is achieved during passage through the dialyzer. The remaining aluminum therefore settles in the bones, causing bone cysts and osteomalacia. Since, after 5 years of dialysis treatment, almost every patient displays more or less significant aluminum deposits in bones and tissue, this results in considerable deterioration of the general health of the patient.

From the DE-OS 40 04 978 it is known to eliminate aluminum ions from the organism in the context of preventive Morbus Alzheimer therapy. This may be achieved by peroral administration of synthetic complexing agents, in particular of hydroxyaromates comprising protective groups. The affinity of the complexing agents with aluminum ions is thereby greater than that of citrate or ATP.

However, major side-effects may occur due to the oral administration of the complexing agents and the systemic effects caused thereby.

Experiments have further already been conducted (Hümpfner, A., "Aluminiumtoxikation bei Niereninsuffizienz", Zuckschwerdt Verlag, Munich 1989) with the object of improving the purification performance of dialyzers with the aid of chelate generators, e.g. desferrioxamine (DFO). Such chelate generators were either administered orally, thus also producing systemic effects, or they were applied with a perfusor, or they were applied intramuscularly (i.m.), slowly intravenously (i.v.), subcutaneously, or also intraperitoneally.

Although good initial results were obtained by the administration of DFO, it was not possible to perform chronic treatment with this method, since DFO proved to be too toxic. It was thus impossible to remove the ingested aluminum directly, i.e. during the next dialysis treatment. It therefore became practice to administer DFO only in certain intervals in the form of cures, during which the aluminum in the bones was mobilized and subsequently removed with the aid of dialysis. The disadvantage of such treatments is that a relatively high concentration of aluminum in the bones must first be achieved and that, during the interval between the administration of DFO and the removal of the Al-DFO complex by means of dialysis (usually on the following day), significant concentrations of aluminum (predominantly in the form of DFO complex) occur in the blood, causing massive side-effects.

As early as 1961, Manira et al. (Am. J. Med. Sci., 242, pp. 32 ff.) already reported experiments concerning the use of tri-sodium citrate for regional anti-coagulation in dialysis treatment.

Avoiding the use of heparin as an anti-coagulant, tri-sodium citrate was introduced into the bloodstream by means of infusion immediately prior to the flow through the dialyzer.

Since no heparin is used at all, this method requires the administration of high doses of tri-sodium citrate to prevent a possible activation of the coagulation system on the foreign surface of the conduction system of the extracorporeal bloodstream and thus ensure safe anti-coagulation.

With the high flow rates of 200–300 ml/min conventionally obtained today, this results in a high level of citrate being introduced into the body of the patient. This may be balanced by intravenous administration of calcium, which, however, represents process-technological problems.

In addition, an excessive introduction of tri-sodium citrate into the blood may result in an undesirable rise of the blood sodium level causing high blood pressure.

The use of citrate during dialysis treatment therefore appeared unadvisable.

In the WO 91/06326 the replacement of heparin by citrate was again dealt with, whereby citrate was introduced into the blood circulation as an anticoagulant, downstream from the dialyzer. To prevent alkaloses resulting from the decomposition of citric acid into $CO_2$ and $H_2O$ in the course of metabolism, complex additional measures were employed in the process described in the WO. A dialyzate having sodium and calcium concentrations below the normal levels was, inter alia, used, as well as a total alkali concentration sufficient to protect against alkaloses.

SUMMARY OF THE INVENTION

In view of the described prior art, the present invention proceeds from the problem of developing an apparatus of the type described above in such manner that it permits removal of aluminum ions during dialysis treatment without giving rise to serious side effects for the patient. Moreover, the invention is to provide solutions which may be used in the apparatus to remove the aluminium ions.

The problem is solved by an apparatus according to the features of the characterizing part of claim 1 and by solutions according to the features of the characterizing parts of claims 20 through 27, for use in said apparatus.

Advantageous embodiments of the apparatus according to the invention are claimed in the respective subordinate claims.

The apparatus according to the invention permits the removal of aluminum ions from whole blood, whereby at least one anti-coagulant and at least one substance for generating a complex compound with the aluminum ions to be removed are introduced into the bloodstream upstream from the semipermeable filter.

The invention thus principally also allows for the complexing agent or agents to also act to complex other metal ions present in the blood. However, the intention is to combine optimal reactivity of the complexing agent with aluminum ions, optimal stability of the complex generated and high selectivity of the complexing process, in particular with regard to aluminum ions.

Nonetheless, apart from effective aluminum ion removal, the principle of the invention also facilitates effective removal of other metal ions present in blood, provided a suitable complexing agent and suitable reaction conditions are selected.

It is, however, preferred to use the system in such manner that its capacity for selective aluminum ion removal is optimized.

It is vital that the substances used in the apparatus according to the invention facilitate sufficiently high metal ion removal, in particular removal of aluminum ions, whilst sufficient coagulation prevention is also provided, including downstream of the semipermeable filter.

Due to the interaction between metal ions and the complexing agent or agents, energetically stable compositions are generated which, as a result of their molecular dimensions and the concentration differential between the bloodstream side and the dialysis side of the filter, diffuse through the filter and can be led off by the dialysis liquid.

The apparatus for removing aluminum ions from blood is advantageously characterised by the fact that the solution complexing the aluminum ions can be precisely dosed with a dosage device, e.g. a pump. A roller pump may, e.g., be used, which is suitably arranged between the source, i.e. the complexing agent reservoir, and the outlet of the source into the blood feeder line of the bloodstream.

The introduction of predetermined quantities of aluminum ion complexing solution is particularly advantageous for two reasons.

Firstly, a dose of suitable complexing agents sufficient to remove the aluminum ions must be introduced, adapted to the activity resp. concentration of the aluminum ions to be removed from the blood, which are usually present not in free, but in complex bound form (e.g. bound to proteins such as albumin or others), adjusted also to the stability of the linkage of the aluminum ion-protein complex possibly already present in the blood and further adjusted to the bloodflow rate in the bloodstream.

Secondly, the quantity of the complexing agent dosage must be limited since, although the complexing agents used in the apparatus according to the invention are generally not toxic, even non-toxic substances added to the blood of the patient may cause disadvantageous side-effects if introduced in too large quantities. Excessive introduction of complexing agent into the blood may, however, not only occur due to an over-dosage not in accordance with the invention, but also by deficient diffusion capacity of the aluminum ion complex. For example, when using a membrane filter it may occur that, despite an adequate complexing rate and sufficient stability of the aluminum ion complex, the latter displays defective membrane passage capacity. The type of complexing agent employed must in this case also be adjusted to the (membrane) filter used.

In a preferred embodiment of the apparatus according to the invention the connection between the blood feeder line and the source of the aluminum complexing solution is arranged on the semipermeable filter, spaced from the connection of the blood feeder line of the bloodstream. This distance serves as a mixing route for the blood and the added aluminum ion complexing solution. The connection point of the blood feeder line and the aluminum complexing solution line is thereby to be arranged so far ahead of the semipermeable filter that thorough mixing of blood and solution can be achieved, taking account of the flow-rate of the blood in the blood feeder line and the inflow rate and volume of the aluminum complexing solution.

Sufficiently thorough mixing is also a precondition of the generation of a complex of aluminum ions and complexing agent, depending on the rate of complex formation, the stability of the complex and possible competing reactions. In particular if flow profiles are formed in the blood feeder line, the adequate length of the mixing route is of vital importance.

Turbulences may be introduced into the flow in the blood feeder line, but it is preferred to provide the semipermeable filter or the inlet connection of the semipermeable filter with a specially constructed mixing connector or a mixing device or mixing chamber, so as to connect the blood line as well as the line connected to the ion complexing solution source with the mixing connector or mixing chamber.

In the latter case, a longer mixing route in the blood feeder line is not required, so that the apparatus as a whole may be more compact. Ultimately, however, adequate mixing before the entry of the bloodstream into the semipermeable filter must always be ensured.

An example of an apparatus suited to effect such mixing is, inter alia, a so-called proportional mixing unit, such as that known to the person skilled in the art from use in dialyzer systems. Dropping chambers or the known mixing analysis systems are also suitable. The dosage into the blood tube system can be effected, inter alia, by means of a controllable roller pump or a controllable injection pump.

All filters which are semipermeable by the aluminum ion complexes respectively to be removed, i.e. which are permeable by the complexes to be removed in one direction only, are suitable as semipermeable filters. Membrane filtering media whose use, e.g. in dialyzers, is known to the expert from the prior art are preferred.

As explained above, it is an important feature of the invention that the aluminum ion complexing agent is used in addition to an anti-coagulant. In addition to precise dosage of the aluminum complexing agent, precise dosage of the anti-coagulant is also preferred in a further embodiment. This is suitably achieved in that a pump is positioned between the blood feeder line and the source of the anti-coagulant connected thereto, with which predetermined quantities of the anti-coagulant may be added into the bloodstream.

The quantity of anticoagulant to be added is determined by the quantity and properties of the blood. Since in some cases the aluminum complexing agent can also act as an anti-coagulant, e.g. by complexing metal ions which are essential to coagulation prevention, the quantity of anti-coagulant which must be used may, depending on the individual situation, be lower than when using only a single anti-coagulant.

If the anti-coagulant is fed to the blood stream further upstream from the semipermeable filter than the potentially also anti-coagulant aluminum ion complexing agent, then the anti-coagulant must at least prevent coagulation of the blood by contact with the foreign surfaces of the tube system of the bloodstream until the also anti-coagulant aluminum ion complexing solution is added.

The mixing location of the anti-coagulant with the blood may, however, also coincide with the mixing position of the aluminum ion complexing solution. Addition of the anti-coagulant upstream of the aluminum complexing agent is, however, preferred.

All substances which are conventionally used to prevent blood coagulation may be used as anti-coagulants, including heparin, himdin and/or prostacyclin, etc.

However, according to the invention, heparin, which prevents blood coagulation in the extracorporeal bloodstream conduction system in known manner, is especially preferred as the anti-coagulant. Since heparin is a polydisperse macro-molecular substance, a higher molecular substantially non-dialyzable heparin fraction with a molecular weight of MW>20,000 is thereby generally used.

All conventionally suitable solutions of an organic or organic complexing agents may be used as aluminum ion complexing solutions. The nature of the complex created is thereby of subsidiary importance. It may be a chelate, a cluster or bridge, sandwich, crown, pod and or similar composition. It is, however, essential that the complex created is dialyzable. The complexing agents include, e.g., EDTA, oxalate, DFO, substantially membranous heparin (heparin capable of passing through a membrane) and/or citrate.

Account must generally be taken of the toxicity or possible side-effects of the complexing agent on the patient. If this, however, is not a key consideration, all named substances are equally employable, depending on the problem respectively to be solved. If toleration by the organism is a vital concern, then the use of citrate, in particular tri-sodium citrate, is considerably preferred.

The use of membranous heparin with a molecular weight of MW<5000 is also preferred.

To simplify the apparatus it is suitable to provide an embodiment wherein the reservoirs of the anti-coagulant and the complexing agent are combined in a joint source. In the context of the present invention this means that the complexing agent and the anti-coagulant can be administered from a single source or reservoir, in the form of a single solution. This, however, is only suitable provided that both substances do not negatively influence each other and as long as the concentrations of the complexing agent and the anti-coagulant can form a substantially constant ratio in the apparatus according to the invention.

If a joint source is provided, it is preferred that the joint source contains predetermined quantities of citrate and heparin to be introduced into the bloodstream in the form of substantially non-dialyzable anti-coagulants.

A further preferred embodiment in the case of a single source is the simultaneous use of substantially non-dialyzable heparin and membraneous heparin.

As indicated above, anti-coagulant substances may also act as complexants and vice versa.

In the special case of heparin, in which a poly-disperse substance provides the option of strongly influencing membrane passage, depending on the molecular weight fraction used, the above-specified preferred combination facilitates the provision of adequate coagulation prevention both upstream and downstream of the semipermeable filter, as well as the desired discharge of aluminum ions.

Apart from the possibility of using only a single joint source and a polymers substance, albeit in different fractions regarding molecular weight, the present invention also provides the further advantageous option of using only one fraction of a poly-disperse substance. In an embodiment of the invention it is therefore preferred to use heparin only in one source. By adding a sufficient quantity of a particularly short-chained heparin (MW<5,000), a sufficiently large quantity of metal ions is discharged from the bloodstream via the dialyzing liquid. The portion of the heparin which is not discharged serves to prevent coagulation downstream of the filter.

The apparatus according to the invention is principally suited for removing a large variety of metal ions from blood, depending on the coplexing agent employed. These metal ions include, inter alia, magnesium ions, calcium ions, aluminum ions, iron ions and/or copper ions. These may either be eliminated from the blood by one complexing agent or a mixture of complexing agents.

However, in view of the comments presented in the introduction, it is especially preferred to remove aluminum ions from blood with the apparatus according to the invention.

If this is done in the course of a dialysis treatment with simultaneous use of citrate as the complexing agent and heparin as the anti-coagulant, then the aluminium-citrate complex as well as possibly present excess citrate are passed to the dialysing liquid together with ureamia toxines and are thus eliminated from the blood.

In this case, it may be preferred for the dialyzing liquid source to contain a dialyzing liquid with metal ion concentrations which may possibly be unintentionally removed from the blood during this process.

If the effect of the complexing agent is not sufficiently specific, metal ions may be resubstituted in this manner.

Since the removal of copper, calcium and magnesium is not desired in a normal dialysis treatment, it is advantageous for the dialysis liquid to contain concentrations of copper, calcium and/or magnesium ions, in particular concentrations of calcium ions, to supplement the respective free ions from the dialyzate which may have been undesirably bound by the complexing agent and thus been discharged through the filter. It is obvious that the ions should be present in sufficient quantity in the dialyzing liquid solution for the purposes of this substitution. In exceptional cases, however, an oral substitution may also be desirable, e.g. to substitute iron ions.

The diffusion of the complexed metal ions from the blood to the dialysis side can occur simply on the basis of concentration differences. However, it may be effectively supported in that an apparatus according to the invention comprises an ultrafiltration pump in the dialyzing liquid duct. Said pump is controllable in such manner that the quantity of ultrafiltrate withdrawn from the bloodstream is no larger than the quantity of fluid fed into the bloodstream by means of the apparatus during the dialysis treatment, including the additional quantities of aluminum complexing agent solution. The ultrafiltration pump is thereby controllable independently of the fact whether metal ion complexing agent solution and anti-coagulant solution are fed from one or two sources.

In its various embodiments the apparatus according to the invention therefore facilitates the performance of a combined anti-coagulating complexing process which substantially differs from the regional citrate anti-coagulation described in the introduction. The regional citrate anti-coagulation must operate with calcium- and magnesium-free dialyzates so as to prevent coagulation in the line or tube system downstream of the dialyzer. In a process with the apparatus according to the invention the concentration of the anti-coagulant (e.g. heparin) is barely reduced and an additional systemic administration of calcium and magnesium is therefore not required.

The invention also concerns solutions for use in the individual embodiments of the apparatus according to the invention. In particular, the invention provides aluminum ion complexing and anti-coagulant solutions characterized by their citrate ion content and their content of substantially non-membraneous heparin. Furthermore, it is advantageous to use a solution according to the invention, which simultaneously comprises dialyzable (membraneous) and substantially non-dialyzable (non-membraneous) heparin. Solutions are also used according to the invention which contain a required amount of membraneous heparin.

The citrate and/or heparin content of the solutions to be used according to the invention may vary within a joint range.

Thus, solutions containing citrate, comprising approximately 40–50 g/l sodium citrate and 14–18 g/l citric acid monohydrate are preferred. Solutions having an approximate content of 44 g/l sodium citrate and 16 g/l acid monohydrate are especially preferred.

Said contents correspond to a citrate concentration of approximately 0.25 M. When the solution is mixed with blood the mixing ratio according to the invention is 1:100 (=25 mM titrate) minimum and 1:5 (=50 mM citrate solution) maximum. If the mixing ratio is lower than 1:100 the complex formation with aluminum ions is no longer ensured. If the mixing ratio is higher than 1:5, then the high citrate concentration in the blood results in the undesirable side-effects mentioned in the introduction. A mixing ratio of approximately 1:7 (=35 mM) is preferred.

The high molecular heparin content of the solutions used according to the invention is between approximately 3 and approximately 200 mg/l. The preferred content is between approximately 30 and 50 mg/l. Especially preferred is a content of approximately 40 mg/l.

High molecular heparin (MW>5,000, preferably MW=20,000) is administered to the patient in a bole unit of 5,000 U (=38.5 mg/l). The blood tube system is likewise prefilted with saline solution of 5000 U per liter. The patient is administered 1000 U per hour to preserve the initial concentration. If the concentration of high molecular heparin is lower than 3 mg/l in the solution to be used according to the invention, coagulation can no longer be reliably prevented. Concentrations higher than 200 mg/l may be toxic.

Low molecular heparin may be contained in the solution to be used according to the invention in a concentration range of approximately 3 mg/l to approximately 60 mg/l. Contents of approximately 30 to 50 mg/l are preferred. A content of approximately 40 mg/l is particularly advantageous. Low molecular heparin (MW<5000, e.g. MW=4500) can, however, also be administered in relatively greater concentrations (up to 600 mg/l) than high molecular heparin.

The construction and the manner of operation of an apparatus according to the invention are explained with reference to the FIGURE.

BRIEF DESCRIPTION OF THE FIGURE

The FIGURE shows a schematic presentation of an embodiment of a dialyzer with the attached tubes.

The dialyzer 10 comprises a semipermeable membrane 20 which separates the dialyzer 10 into a blood side 30 and a dialyzate side 40. The blood side 30 and the dialyzate side 40 are leakproof with respect to each other and connected only by the semipermeable membrane 20.

A dialyzing liquid source 50 is connected via a duct 60 with an inlet 70 of the dialyzate side of the dialyzer 10. The duct 80 is connected to an outlet 90 of the dialyzate side 40 of the dialyzer 10.

A blood feeder duct 100 is connected to an inlet 110 of the blood side 30 of the dialyzer 10. A blood outlet duct 120 is connected to an outlet 130 of the blood side 30 of the dialyzer 10. A pump 140 is arranged upstream of the dialyzer 10 in the blood feeder duct 100.

Apart from the dialysis liquid source 50, two further sources are shown in the FIGURE. An anti-coagulant source 150 is connected to the blood feeder duct 100 via a line 160, and a further source 170 of a metal ion complexing agent is also connected via a line 180 to the blood feeder duct 100, but downstream of source 150. The connection point of the source 150 with the blood feeder duct 100 is designated as 190 and the connection point of the source 170 with the blood feeder duct 100 is designated as 200. Both between the source 150 and connection point 190 and between the source 170 and the connecting point 200, a pump 210 and a pump 220, respectively, is interposed. An ultrafiltration pump 230 is arranged in line 80 downstream of the dialyzer 10.

The apparatus is operated as follows: Whole blood is circulated in the extracorporeal bloodstream, consisting of duct 100, pump 140, blood side 30 of the dialyzer 10 and duct 120. This blood may be taken, e.g. from a dialysis patient. In counterflow thereto, the dialysis liquid is passed with the aid of ultrafiltration pump 230 from source 50 via ducts 60 and 80 as well as the dialysis side 40 of the dialyzer 10 along the membrane 20. Due to the differential concentrations of the whole blood and the dialyzate solution, material exchange occurs along the semipermeable membrane 20 by diffusion. Downstream of the pump 140 at the mixing point 190 heparin is introduced into the blood feeder duct 100 as an anti-coagulant from source 150 via duct 160 and pump 210. Downstream from connection point 190, but with a sufficient mixing route 200-110, a predetermined quantity of tri-sodium citrate is added from source 170 via duct 180 and pump 220 as a complexing agent. Heparin thereby prevents coagulation in the extracorporeal bloodstream, whilst citrate complexes and thus renders dialyzable the aluminum ions contained in the blood.

The effectiveness of the apparatus is demonstrated with the aid of the following example:

EXAMPLE 6 liters of fresh bovine blood are mixed with app. 6000 U (=1000 U/l=7.7 mg) high molecular heparin (heparin sodium MW 20000, FRESENIUS AG) and with a commercial ACD solution (anti-coagulant solution as a conservation additive for fresh blood; contains acidum citricumpurum 2.5%, dextrose 2.34% and sodium citricum 2.16%) in a ratio of 7:1 and is adjusted to a hematocrit of 30 with normal saline solution. The blood is thermosrated at 37° C. whilst being stirred. 20 mg aluminum (in the form of aluminum sulfate) are dissolved in 1 liter normal saline solution and app. 10 ml/l of this solution are added to the blood (corresponding to 0.2 mg/l blood). The blood is stirred for another 30 min at 37° C. A bloodstream is created comprising a reservoir for 3 l blood, a source for 3 l normal saline solution and a dialyzer (in this case a HEMOFLOW F60). The tube system comprises the following parts (in flow direction):

a tube piece from the reservoir of the normal saline solution to a pump section, a pump section embedded in a roller pump, a tube piece from this pump section to the dialyzer, a dialyzer through whose dialysis liquid area 500 ml normal saline solution of 37° C. flow, a tube piece from the dialyzer back to the source.

The velocity of the roller pump is set at 50 ml/min and the system is filled bubblefree.

The pump is then stopped, the inlet of the tube system is inserted in the source of the heparinized bovine blood and the outlet is inserted in an empty vessel. The pump is started and blood is pumped through the system at 50 ml/min. After 10 minutes, samples are simultaneously taken at the inlet and the outlet of the tube system (sample cit50in and cit50out). The flow rate is then raised to 200 ml and after further 10 minutes, samples are again taken simultaneously at the inlet and the outlet (samples cit200in and cit200out). A sample of the dialyzing fluid is taken before the inlet into the dialyzer and designated as citdial.

Comparative Example 6 liters of fresh bovine blood are mixed with 125,000 units heparin (heparin sodium MW 20,000, FRESENIUS AG) in 250 ml normal saline solution and adjusted to a hematocrit of 30 with further normal saline solution. The blood is thermosrated at 37° C. whilst being stirred. 20 mg aluminum (in the form of aluminum sulfate) are dissolved in 1 liter of normal saline solution and approximately 10 ml/l (corresponding to 0.2 mg/l blood) are added. The blood is stirred for further 30 min at 37° C.

The further progress of the experiment corresponds exactly to that of the example. The samples are designated as hep50in and hep50out and hep200in and hep200out, respectively, and the control measurement of the dialysis liquid used as hepdial.

Results

|  | hepdial | hep50in | hep50out | hep200in | hep200out |
|---|---|---|---|---|---|
| ppm/l Al | <2 | 146 | 80 | 140 | 83 |
|  | citdial | cit50in | cit50out | cit200in | cit200out |
| ppm/l Al | <2 | 131 | 40 | 145 | 52 |
| anti-coag. | heparin |  | citrate |  |  |
| blood-flow | 50 ml/min | 200 ml/min | 50 ml/min | 200 ml/min |  |
| purification performance | 41% | 40.7% | 69.4% | 64.1% |  |

The comparison of the purification performance shows that the combined use of citrate ions and heparin is markedly superior.

While the invention has been described in terms of its preferred embodiments, those skilled in the art will recognize that the invention can be practiced with modifications within the spirit and scope of the appended claims.

I claim:

1. A method for treating a person having aluminum intoxication, comprising:

leading a flow of blood along one side of a semipermeable membrane of a dialyzing filter and a flow of dialyzing fluid along a second side of said semipermeable membrane;

mixing a non-dialyzable anti-coagulant and an aluminum ion complexing agent which complexes aluminum with said blood upstream of said dialyzing filter, said mixing step producing a mixture containing said blood, said non-dialyzable anticoagulant, said aluminum ion complexing agent and aluminum ion complexes formed from said aluminum ion complexing agent and aluminum ions present in said blood;

passing said mixture through said dialyzing filter; and removing said aluminum ion complexes through said semipermeable membrane.

2. The method of claim 1 wherein said mixing step includes the steps of:

selecting said non-dialyzable anticoagulant to be non-dialyzable heparin; and selecting said aluminum ion complexing agent to be a solution of citrate.

3. The method of claim 1 wherein said mixing step includes the steps of:

selecting said non-dialyzable anticoagulant to be non-dialyzable heparin; and selecting said aluminum ion complexing agent to be dialyzable heparin.

4. A method for removing aluminum from blood, comprising the steps of:

adding an anticoagulant to blood;

adding a complexing agent which complexes aluminum to said blood, wherein at least one of said anticoagulant and said complexing agent is a non-citrate compound;

allowing said complexing agent to intermingle with said blood and complex with aluminum present in said blood;

separating complexes of said complexing agent and said aluminum from said blood through a semipermeable membrane; and recovering said blood.

5. The method of claim 4 wherein both said adding steps are performed simultaneously.

6. The method of claim 4 wherein said adding an anticoagulant step is performed prior to said adding a complexing agent step.

7. The method of claim 4 wherein both said adding, said allowing, said separating, and said recovering steps are performed in series in a circuit.

8. The method of claim 4 wherein said separating step includes the steps of supplying a mixture of said blood, said complexing agent, said anticoagulant, and complexes of aluminum in said blood and said complexing agent to a first side of said semipermeable membrane;

supplying a dialysate to a second side of said semipermeable membrane; and allowing said complexes of aluminum in said blood and said complexing agent to diffuse through said semipermeable membrane into said dialysate.

9. The method of claim 8 wherein said supplying of dialysate step includes the use of a dialysate with metal ions present in said dialysate.

10. A method for removing aluminum from blood, comprising the steps of:

adding at least one non-citrate compound to blood in an amount effective in preventing coagulation of blood and capable of complexing aluminum;

allowing said at least one non-citrate compound to intermingle with said blood and complex with aluminum present in said blood;

separating complexes of said at least one non-citrate compound being capable of complexing aluminum and aluminum present in said blood from said blood through a semi-permeable membrane; and recovering said blood.

11. A method as in claim 10, wherein said non-citrate compound is dialyzable heparin.

* * * * *